(12) United States Patent
Wu

(10) Patent No.: US 7,531,810 B2
(45) Date of Patent: May 12, 2009

(54) INTEGRATED HALF-BEAM PROFILE MEASUREMENT AND POLAR PROFILE FOR CIRCULAR RADIATION FIELD SYMMETRY ASSESSMENT

(75) Inventor: Xiaodong Wu, Miami, FL (US)

(73) Assignee: James G. Schwade, Miami, FL (US), part interest ( * ) Notice: Subject to any disclaimer, the term of this patent is extended or adjusted under 35 U.S.C. 154(b) by 467 days.

(21) Appl. No.: 11/499,380

(22) Filed: Aug. 4, 2006

(65) Prior Publication Data
US 2007/0029508 A1 Feb. 8, 2007

Related U.S. Application Data

(60) Provisional application No. 60/705,357, filed on Aug. 4, 2005.

(51) Int. Cl.
*G01K 1/08* (2006.01)
*H01J 3/14* (2006.01)
*H01J 3/26* (2006.01)

(52) U.S. Cl. .............. 250/375; 250/491.1; 250/583; 250/585; 250/378; 600/1; 600/3; 600/417; 600/114; 600/410; 600/407; 600/427; 607/130; 607/129; 607/108; 607/131; 607/14; 378/65; 378/158; 378/205; 378/123; 378/119; 378/121; 378/64; 378/116; 378/108; 378/207

(58) Field of Classification Search ............ 250/492.23, 250/491.1, 397, 484.4, 583, 585, 305, 399, 250/378; 600/1, 3, 417, 114, 410, 407, 427; 607/130, 129, 108, 131, 14; 438/48; 378/65, 378/158, 205, 123, 119, 121, 64, 116, 108, 378/207
See application file for complete search history.

(56) References Cited

U.S. PATENT DOCUMENTS 7,356,120 B2 * 4/2008 Main et al. .................... 378/65

* cited by examiner

*Primary Examiner*—Jack I Berman
*Assistant Examiner*—Meenakshi S Sahu
(74) *Attorney, Agent, or Firm*—Pinkert Law Firm, P.A.

(57) ABSTRACT

A method for routine monitoring and quality assurance of field asymmetry of high energy circular radiation beam producing equipment. The quality assurance process of field symmetry for devices such as stereotactic radiosurgery (SRS) systems is simplified by directly measuring the integration of the half-beam profile. The method of the invention provides that the field symmetry is obtained by positioning the tip of an ion chamber, with a collecting length approximately half the diameter of the beam, at the central axis of the beam, and rotating the ion chamber at varying angular positions, acquiring and comparing readings at desired angular positions. Each pair of readings from positions 180 degrees opposed from each other, are plugged into the equation, Asymmetry=2 (R1−R2)/(R1+R2) to compute asymmetry.

1 Claim, 11 Drawing Sheets

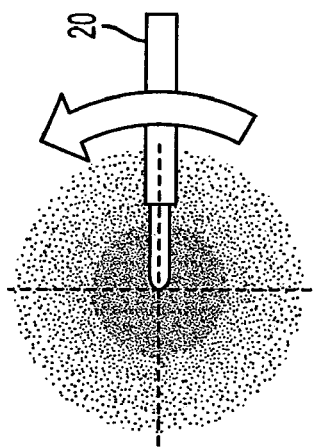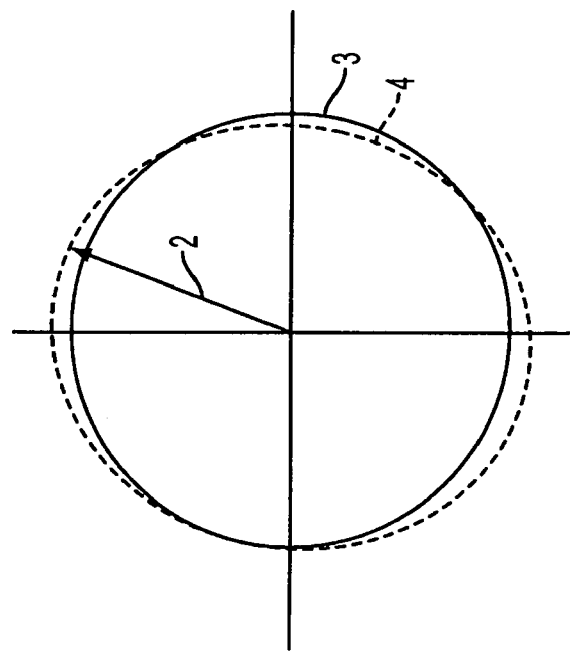
FIG. 4A
FIG. 4B

INTEGRATED HALF-BEAM PROFILE MEASUREMENT AND POLAR PROFILE FOR CIRCULAR RADIATION FIELD SYMMETRY ASSESSMENT

CROSS-REFERENCE TO RELATED APPLICATIONS

This application claims the benefit of U.S. Provisional Application No. 60/705,357, filed Aug. 4, 2005. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to the field of quality assurance (QA) of high energy circular radiation beam producing equipment. For example, the invention relates to high energy (MeV) X-ray producing systems and the ability to monitor the symmetry of the X-ray beam.

BACKGROUND OF THE INVENTION

Although not limited to medical treatment, circular radiation fields are often used in stereotactic radiosurgery (SRS) systems, such as Cyberknife™ or X-knife™. The dimensions of circular radiation fields used in SRS systems are relatively small and the effects of a flattening filter are small. The Cyberknife™ SRS system does not use any flattening filter. In linear accelerators used for conventional radiation therapy field asymmetry is defined as the percentage difference of any pair of points situated symmetrically with respect to the central axis. However, for small circular radiation fields like those produced from the Cyberknife™, the field asymmetry is defined as the percentage difference of two halves of the integrated profile, FIG. 1, where, $$\text{Asymmetry} = 2(A1-A2)/(A1+A2), \quad \text{(Equation 1)}$$

Prior to this invention, circular radiation beam field symmetry assessment was accomplished either by film analysis, or by analyzing the beam profile acquired by scanning the entire field with an ion chamber or solid state detector system. In the above two methods, the field symmetry is obtained by comparing the integration of data points comprising each half-beam profile. The acquisition process of these data points comparison methods is rather lengthy. The objective of this invention is to obtain the field symmetry of circular radiation beams by directly measuring the integration of the half-beam profile, and thus simplify the assessment and quality assurance (QA) process in devices such as SRS linacs (Ref. 1, 2).

This invention provides an efficient and more convenient method for monitoring the field symmetry of circular radiation beams by directly measuring the integration of the half-beam profile.

SUMMARY OF THE INVENTION

The present invention provides a method for routine monitoring and quality assurance of field asymmetry of high energy circular radiation beam producing equipment. It is the object of the invention to simplify the QA process of devices such as SRS linacs by obtaining the field symmetry by directly measuring the integration of the half-beam profile.

BRIEF DESCRIPTION OF THE DRAWINGS

In describing the invention, reference will at times be made to the accompanying drawings in which:

FIG. 4A is a diagram that illustrates the measurement geometry of the polar profile;

FIG. 4B is a diagram of the polar profile, in which radius represents the magnitude of the measurement at an angular position, resulting from the measurement in FIG. 4A;

DETAILED DESCRIPTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

The details of one or more embodiments of the invention are set forth in the accompanying drawings and the description below. Other features, objects, and advantages of the invention will be apparent from the description and drawings, and from the claims.

Figure 1:
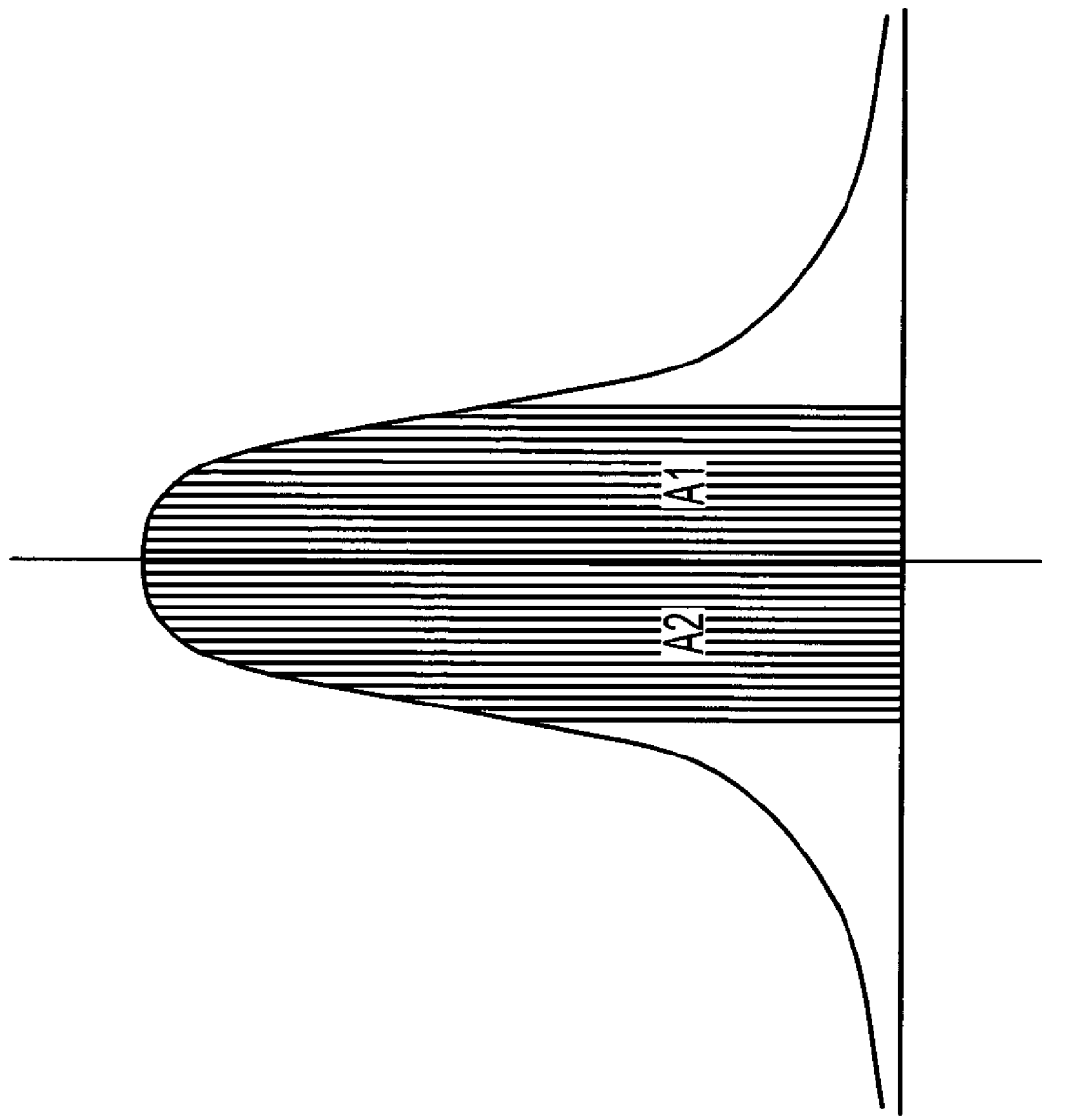
FIG. 1 represents a typical circular beam profile, where A1 and A2 represents the integration of each half-beam profile as expressed in Equation 1.
Figure 2B:
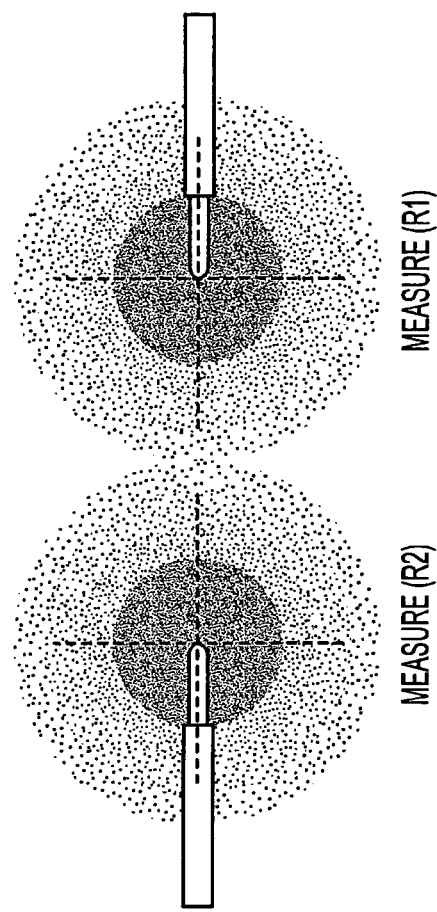
FIG. 2B represents the physical placement of the ion chamber in relation to the circular radiation beam.
Figure 2A:
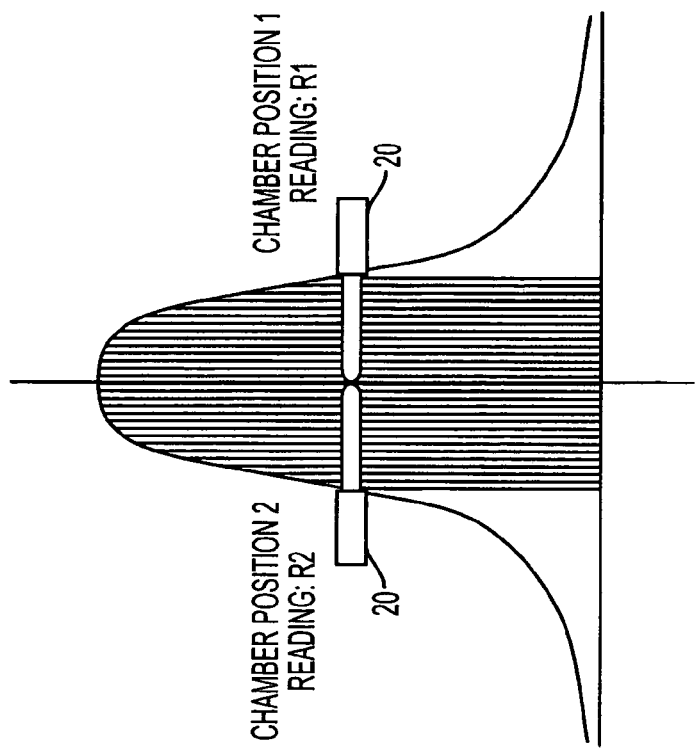
FIG. 2A demonstrates the principle and geometry of direct beam measurement using an ion chamber.

The circular radiation beam asymmetry is defined based on the area ratios of integrated half-beam profiles from the central axis (100%) to the 50% fall-off point. This is illustrated in FIG. 1, where Asymmetry is defined by Equation 1 and where A1 and A2 are 100%-50% half profile integrations. The principle of asymmetry measurement as expressed is based on the assumption that if the ion chamber's 20 collecting length or volume lays across the half-beam, its readings, R1 and R2, as shown in FIGS. 2A, 2B, would represent a good approximation of the calculated area, A1 or A2, as shown in FIG. 1, from a profile. Thus the asymmetry can be rewritten based on these readings as, Asymmetry=$2(R1-R2)/(R1+R2)$ (Equation 2)

A typical 0.6 cc Farmer-Type ion chamber 20 has an effective collecting length of about 2.5 cm. For a circular radiation field with a diameter of 5.0 cm, by placing the tip of the ion chamber at the field central axis, the ion chamber reading would reflect the integrated exposure, or dose of the half-beam profile, and as a consequence of A1 and A2 in Equation 1 being substituted with R1 and R2, asymmetry is expressed by Equation 2, FIGS. 1, 2A, 2B.

Figure 3:
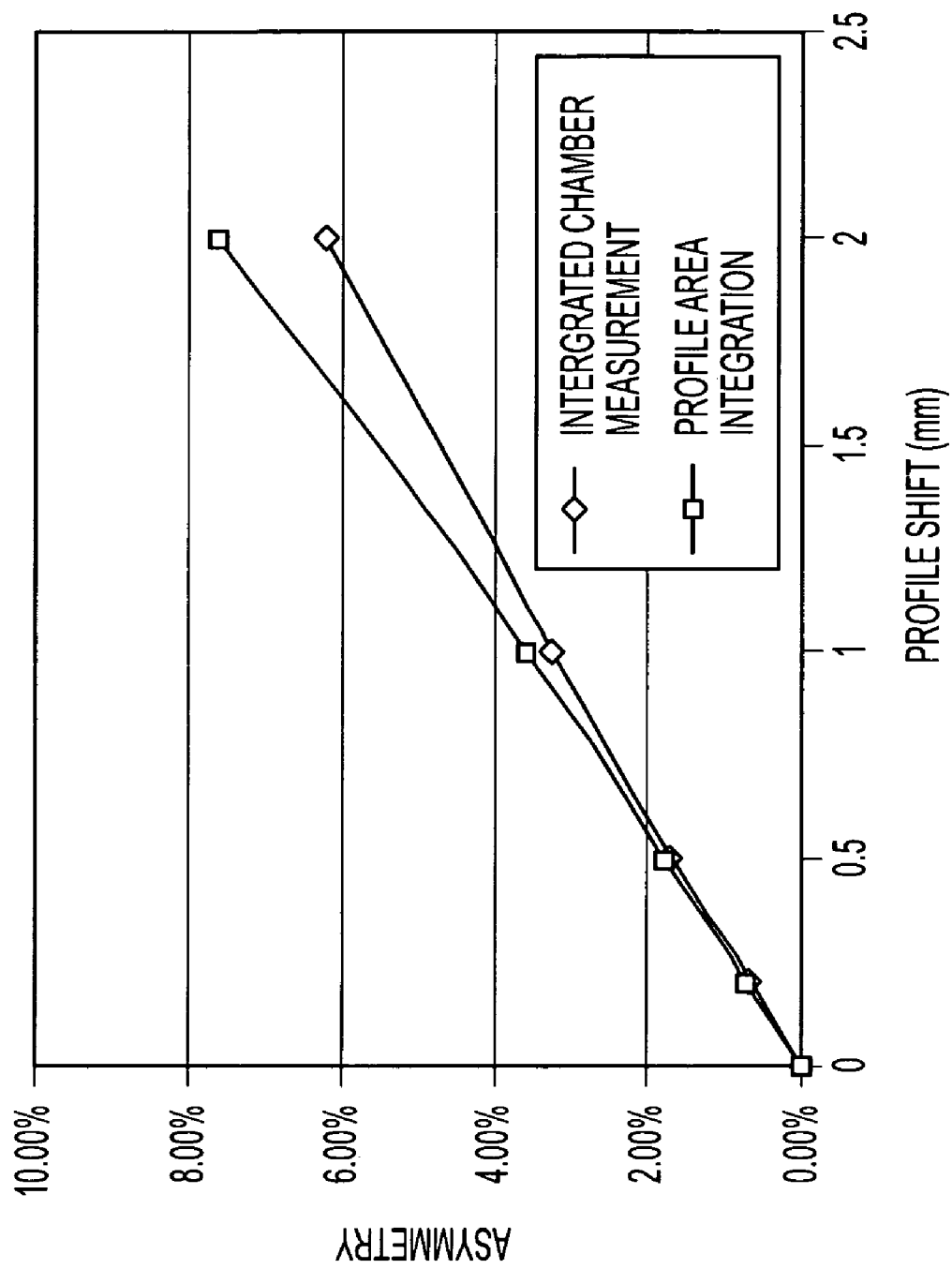
FIG. 3 is a graph comparing the sensitivity of the method of the invention and the conventional method for field symmetry assessment.

The method was tested on a Cyberknife™ unit by shifting the radiation field of a 5.0 cm collimator, in relation to measurement setup, to create field asymmetry. FIG. 3 shows a comparison of the field asymmetry obtained by the new method, as computed by Equation 2, and the conventional method as computed by Equation 1, with respect to different amounts of profile shift. The result shows that the new method, using the preferred embodiment, is sensitive to about a 0.2 mm of the profile shift. The advantage of this method is that there is no need to obtain a full profile in order to calculate the integrated half-beam profile. The results also show that up to 2% beam asymmetry can be accurately detected by the method of the invention. When the value of beam asymmetry is over 2%, the method of the invention overestimates the asymmetry, FIG. 3, which is a conservative safe guard.

The method can be used to assess the whole field symmetry of a circular radiation field by rotating the ion chamber tip around the field central axis with the ion chamber tip fixed at the field central axis as shown in FIG. 4A. The result of this measurement can be presented by the polar profile, as shown in FIG. 4B, in which the magnitude of measurement from the ion chamber at corresponding angular positions is represented by the radius 2. If the beam is isotropically symmetrical, one would obtain a perfect circular or unity polar profile 3, as shown in FIG. 4B. Any deviation from the unity polar profile is an indication of field asymmetry 4, as shown in FIG. 4B. The polar profile as in FIG. 4B, can be used to efficiently adjust the beam because it represents the beam symmetry of the entire field.

The polar profile can be obtained not only in an integrated mode as described above but also in a singular mode. The singular mode of a polar profile can be achieved by placing a micro detector at a certain distance from the beam central axis and rotating the detector around the beam central axis. Although the field symmetry derived from the singular mode of measurement no longer falls into the same definition as the integrated method, it is obvious to one skilled in the art that both the integrated mode and the singular mode of polar profile are effective for the field symmetry assessment.

Figure 5:
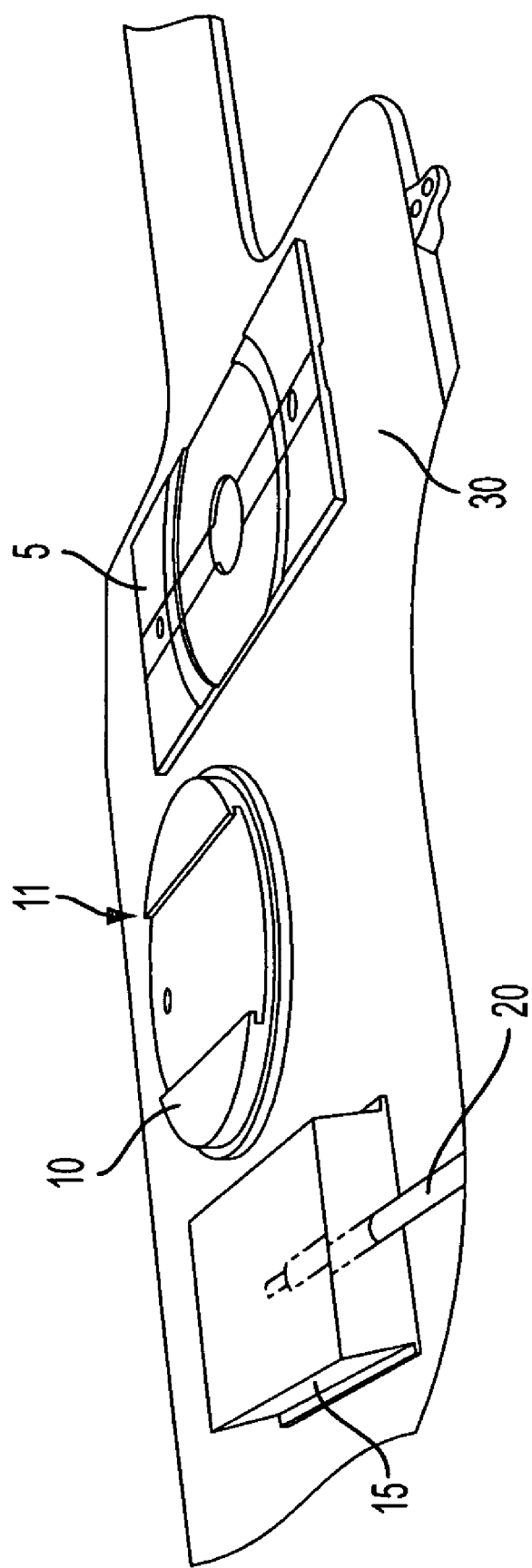
FIG. 5 is a diagram of the unassembled components of the integrated beam QA Platform.
Figure 6:
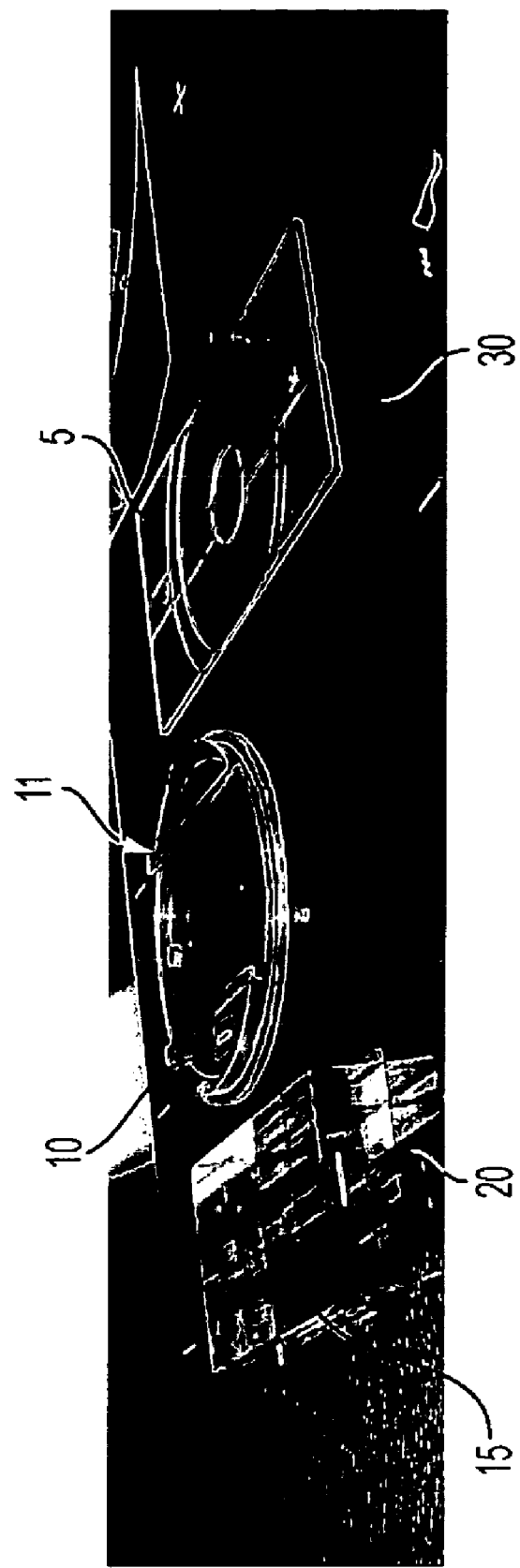
FIG. 6 is a photograph depicting FIG. 5.

The present invention is directed at monitoring the field symmetry of circular radiation beams, such as in X-ray based or charged particle based SRS systems. The invention is implemented by using an Integrated Beam QA Platform ("QA Platform"). With reference to FIGS. 5 and 6, the QA Platform is comprised of the following: a table-mount base 5; a rotating platform 10 with grooves 11 for assembly with a sliding chamber slab 15, and an ion chamber 20. These components are assembled for use with any existing equipment for SRS systems.

Figure 7B:
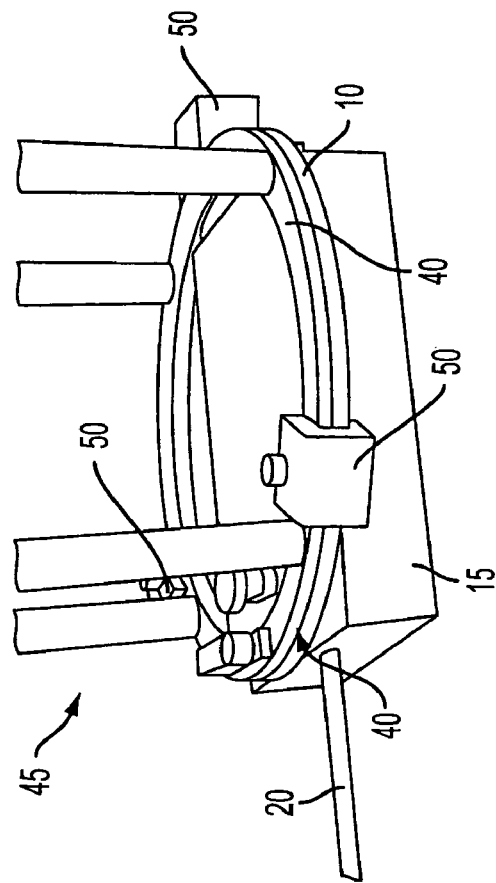
FIG. 7B is a diagram of a complete assembly of the QA Platform in the preferred, Bird Cage embodiment.
Figure 7A:
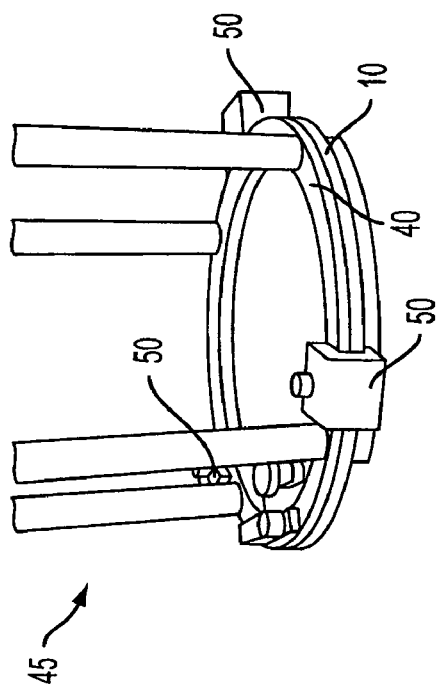
FIG. 7A is a diagram of a partial assembly of the QA Platform in the preferred, Bird Cage embodiment.

In the preferred embodiment, FIGS. 7A and 7B, when the invention is being used with the Cyberknife™, the QA Platform is mounted to a Bird Cage 45, FIGS. 7A, 7B. The Bird Cage 45 is a simple device designed by the manufacturer of the Cyberknife™, which is used to mount a radiation detector in a fixed position of approximately 80 cm from the radiation source, for radiation output measurement. The Bird Cage 45 consists of a rigid metal frame with a distal end 40 that attaches to the QA Platform, as shown in FIGS. 7A, 7B, and a proximal end that attaches to the linear accelerator. One of ordinary skill in the art to which this invention belongs is familiar with the components and function of the Bird Cage and/or variations thereof. The Bird Cage 45 requires a slight modification in order to work with the QA platform and function accurately to bring about the desired results of the invention.

With the slight modification of the Bird Cage 45, the rotating platform 10 is attached to the Bird Cage 45 at the distal end 40 using three supporting adaptors 50, FIGS. 7A and 7B. The design allows the centering of the rotating platform 10 to the beam central axis.

Figure 8B:
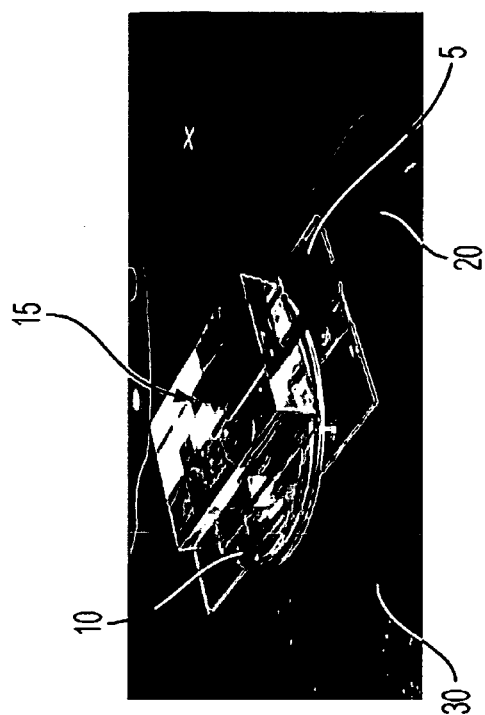
FIG. 8B is a diagram of a complete assembly of the QA Platform Table-Mount embodiment.
Figure 9B:
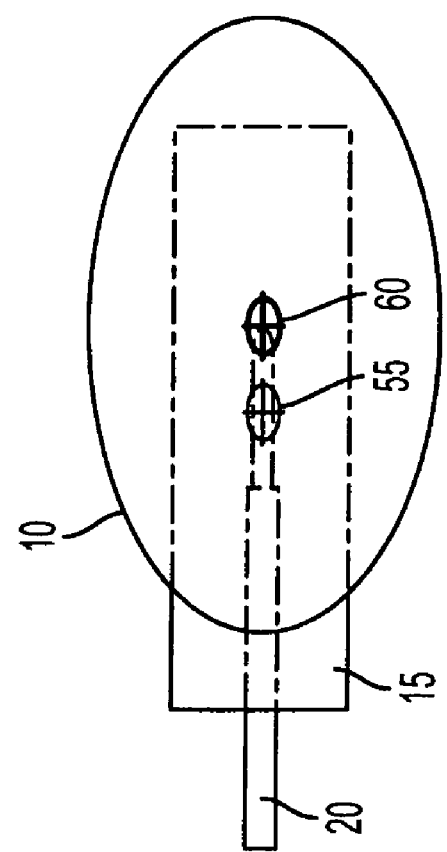
FIG. 9B depicts a top view (beam-eye view) of the position of the ion chamber in the chamber slab in relation to the central axis.
Figure 9A:
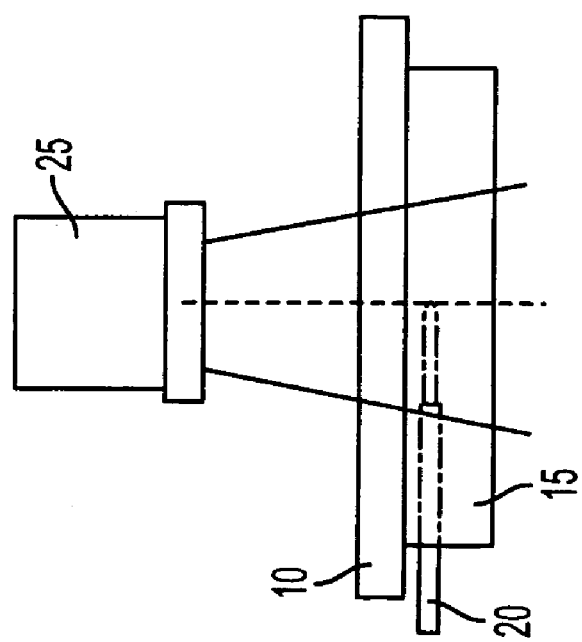
FIG. 9A depicts a side view position of the ion chamber in the sliding chamber slab in relation to the central axis.
Figure 10A:
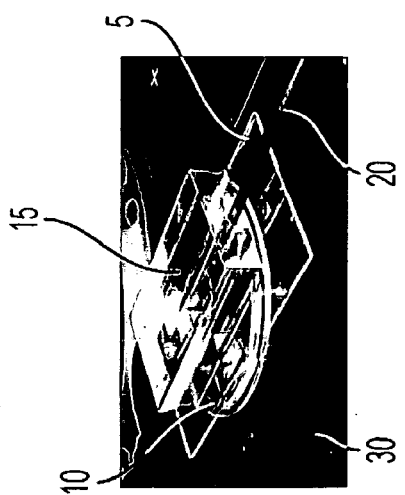
FIGS. 10A, 10B, and 10C are photographs showing three angular positions of rotation about the central axis in the Table-Mount embodiment of the invention.
Figure 10B:
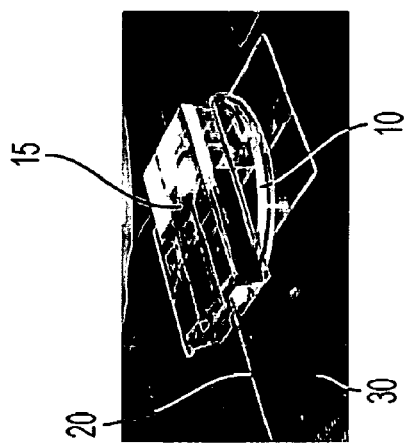
Figure 10C:
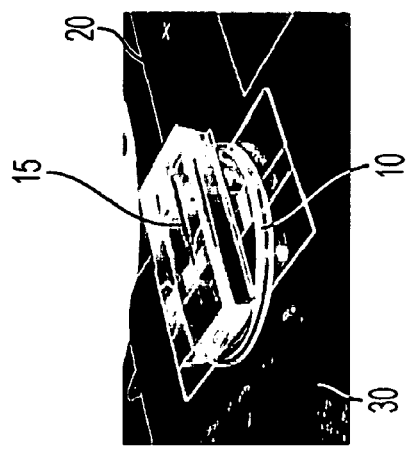
Figure 11C:
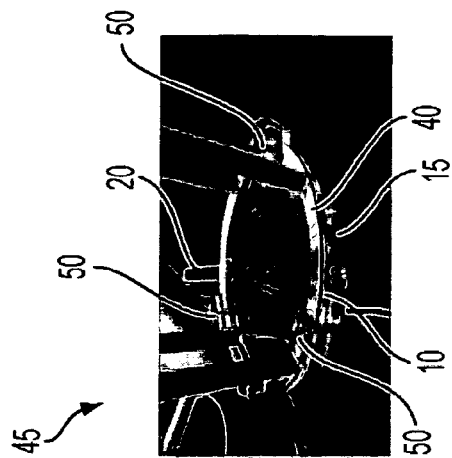
FIGS. 11A, 11B, and 11C are photographs showing three angular positions of rotation about the central axis in the preferred, Bird Cage-Mount embodiment of the invention.
Figure 11B:
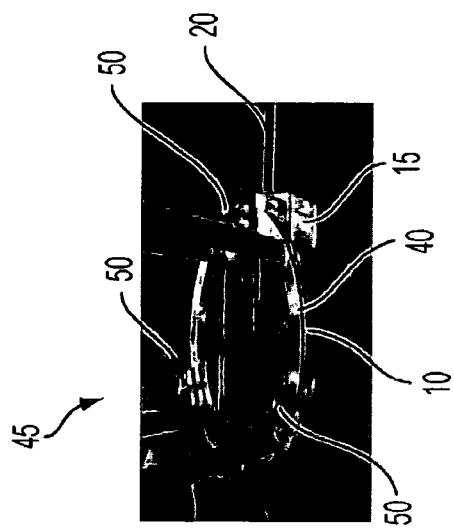
Figure 11A:
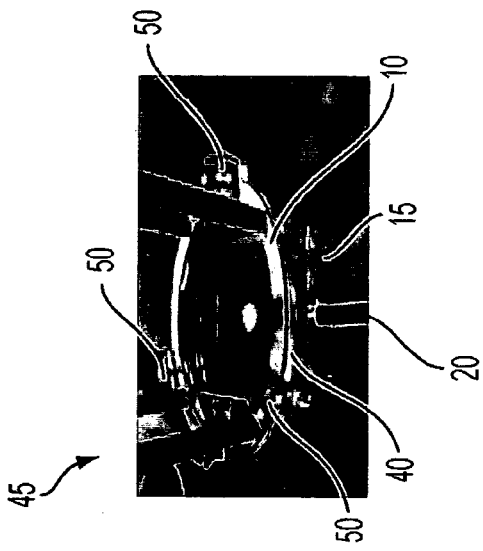

Once the rotating platform 10 is aligned with the beam, the sliding chamber slab 15 can then glide into the grooves 11 of the rotating platform 10, FIG. 8B. There are two alignment markers 55, 60 on the sliding chamber slab 15, as shown in FIG. 9B, allowing alignment of the ion chamber 20 center and the ion chamber 20 tip to the beam central axis.

Figure 8A:
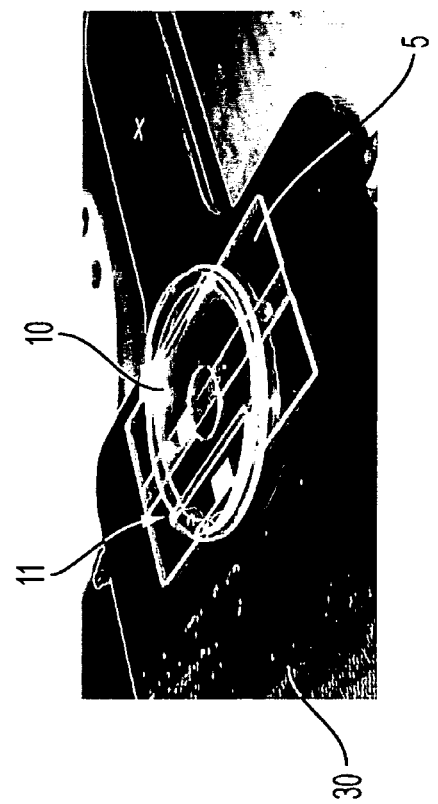
FIG. 8A is a diagram of a partial assembly of the QA Platform in Table-Mount embodiment.

In another embodiment, the QA Platform is mounted on the treatment table 30 for a SRS system, hereinafter referred to as the Table-Mount embodiment, FIGS. 8A and 8B. For the Table-Mount embodiment, first, the table-mount base 5 is rigidly attached to the treatment table 30, then the rotating platform 10 is fitted into to the table-mount base 5, FIG. 8A. The assembly is completed by inserting the sliding chamber slab 15 into the grooves 11 on the rotating platform 10, ensuring proper alignment of the components, FIG. 8B. The Table-Mount embodiment requires robot manipulation to align the central axis of the radiation beam to the QA platform.

Upon complete assembly of the QA Platform in the preferred, Bird-Cage Mounted embodiment, the Table-Mounted embodiment, or any other embodiment that is obvious to one of ordinary skill in the art to which this invention belongs, the assessment of the field asymmetry of circular beams can be undertaken.

The circular radiation beam asymmetry is monitored after the assembly of the QA Platform by rotating the tip of the ion chamber 20 at varying angular positions, and thereby obtaining the integrated half-beam profile, FIGS. 9A, 9B, 10A, 10B, 10C, 11A, 11B, and 11C. The integrated half-beam profiles are collected in pairs, with each member of a pair being 180 degrees from the other. The asymmetry is calculated from the paired readings, R1 and R2, using Equation 2, as shown in FIGS. 2A and 2B.

Both the preferred, Bird Cage-Mount embodiment and the Table-Mount embodiment allow free rotation of the ion chamber orientation, FIGS. 10A, 10A, 10B, 10C, 11A, 11B, and 11C. To perform beam field asymmetry measurements, use alignment markers 55, 60 to position the tip of the ion chamber 20 at the center of the beam, FIGS. 9A and 9B; and utilizing a 5.0 cm collimator 25 with the SRS system, acquire readings at desired angular positions as shown in FIGS. 10A, 10B, 10C, 11A, 11B, and 11C; finally use the equation, Asymmetry=2(R1−R2)/(R1+R2) to compute asymmetry for each 180° position pair obtained from the readings.

The contents of all patents, patent applications, published articles, books, reference manuals and abstracts cited herein are hereby incorporated by reference in their entirety to more fully describe the state of art to which the invention pertains.

As various changes can be made in the above-described subject matter without departing from the scope and the spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

EQUIVALENTS

Those skilled in the art will recognize, or be able to ascertain using no more than routine experimentation, many equivalents to the specific embodiments of the invention described herein. Such equivalents are intended to be encompassed by the claims.

REFERENCES

Reference is made to the following journal articles and other references (e.g. textbooks) that contain definitions and methods and means for carrying out basic techniques, encompassed by the present invention.
1. Comprehensive QA for Radiation Oncology, AAPM TG No. 40, Medical Physics, 21(4), 1994
2. Stereotactic Radiosurgery, AAPM TG No. 42, American Association of Physicists in Medicine, June 1995

What is claimed is:

1. A method for determining circular radiation beam symmetry, which comprises:
   a. using an ion chamber with a collecting length that is approximately equal to one-half of the field size;
   b. placing the tip of the ion chamber at the field's central axis;
   c. rotating the ion chamber in an arc perpendicular to the field central axis while maintaining the tip of the ion chamber in the field's central axis;
   d. acquiring the ion chamber's readings at various angular positions on the rotational arc;
   e. obtaining field asymmetry by comparing the measurements taken at various angular positions on the rotational arc.

* * * * *